United States Patent
AlSofi

(10) Patent No.: US 9,200,996 B2
(45) Date of Patent: Dec. 1, 2015

(54) METHOD FOR DISPERSION AND ADSORPTION COEFFICIENT ESTIMATION USING AN ANALYSIS OF PRESSURE TRANSITION DURING A VISCOSITY-SWITCH

(71) Applicant: Saudi Arabian Oil Company, Dhahran (SA)

(72) Inventor: Abdulkareem Mohamad AlSofi, AlKhobar (SA)

(73) Assignee: Saudi Arabian Oil Company, Dhahran (SA)

( * ) Notice: Subject to any disclaimer, the term of this patent is extended or adjusted under 35 U.S.C. 154(b) by 462 days.

(21) Appl. No.: 13/861,147

(22) Filed: Apr. 11, 2013

(65) Prior Publication Data

US 2014/0109652 A1     Apr. 24, 2014

Related U.S. Application Data

(60) Provisional application No. 61/624,074, filed on Apr. 13, 2012.

(51) Int. Cl.
    *G01N 15/00*     (2006.01)
    *G01N 15/08*     (2006.01)
    (Continued)

(52) U.S. Cl.
    CPC .......... *G01N 15/0826* (2013.01); *G01N 15/088* (2013.01); *G01N 33/24* (2013.01); *H04N 5/2257* (2013.01); *G01N 2015/0873* (2013.01); *H04N 21/4223* (2013.01)

(58) Field of Classification Search
    CPC ............ G01N 15/0826; G01N 15/088; G01N 2015/0873
    See application file for complete search history.

(56) References Cited

U.S. PATENT DOCUMENTS

| | | |
|---|---|---|
| 4,424,487 A | 1/1984 | Lauffer |
| 4,489,593 A | 12/1984 | Pieters et al. |

(Continued)

FOREIGN PATENT DOCUMENTS

| | | |
|---|---|---|
| DE | 3218674 A1 | 11/1983 |
| DE | 3218674 A1 | 11/1983 |

(Continued)

OTHER PUBLICATIONS

Alkindi, A., et al., "Investigation of Longitudinal and Transverse Dispersion in Stable Displacements with a High Viscosity and Density Contrast Between the Fluids," XP-055074115, Journal of Contaminant Hydrology, Mar. 1, 2011, pp. 170-183, vol. 120-121, www.elsevier.com/locate/jconhyd, Elsevier B.V.

(Continued)

*Primary Examiner* — Paul West
(74) *Attorney, Agent, or Firm* — Bracewell & Giuliani LLP; Constance G. Rhebergen; Brad Y. Chin

(57) ABSTRACT

Disclosed is a method for estimating porous-media longitudinal dispersion and adsorption coefficients. According to various embodiments of the invention, a method for estimating porous-media longitudinal dispersion coefficients is provided, which includes introducing a pure phase component though a porous medium, and introducing a component having a same phase as the pure phase component through the porous medium. The component includes a viscosifying agent having a non-linear viscosity-concentration dependence. The method further includes measuring, using a permeability analyzer, a pressure drop across the porous medium after each introduction at a plurality of intervals over a period of time. Further, the method includes determining, using the measured pressure drops, a pressure transition, and analyzing the pressure transition across the porous medium to determine a dispersion coefficient for the porous medium.

13 Claims, 12 Drawing Sheets

(51) Int. Cl.
*G01N 33/24* (2006.01)
*H04N 5/225* (2006.01)
*H04N 21/4223* (2011.01)

(56) References Cited

U.S. PATENT DOCUMENTS

| | | | |
|---|---|---|---|
| 4,576,723 | A | 3/1986 | Eisenlauer |
| 4,709,759 | A | 12/1987 | Bock |
| 4,719,423 | A | 1/1988 | Vinegar |
| 5,269,180 | A | 12/1993 | Dave |
| 5,544,520 | A | 8/1996 | Graf et al. |
| 6,740,625 | B1 * | 5/2004 | Audibert et al. ......... C09K 8/06 507/136 |
| 7,272,973 | B2 | 9/2007 | Craig |
| 8,087,292 | B2 | 1/2012 | Voelker |
| 2008/0127717 | A1 | 6/2008 | Lesieur |

FOREIGN PATENT DOCUMENTS

| | | |
|---|---|---|
| GB | 2127559 A | 4/1984 |
| JP | 2012-047498 A | 3/2012 |
| JP | 2012047498 A | 3/2012 |

OTHER PUBLICATIONS

Peters, E. J., et al., "A Look at Dispersion in Porous Media Through Computed Tomography Imaging," XP-055074113, Journal of Petroleum Science and Engineering, Jul. 1, 1996, pp. 23-31, vol. 15, Elsevier Science B.V.

PCT International Search Report and the Written Opinion of the International Searching Authority dated Aug. 14, 2013, International Application No. PCT/US2013/036076; International Filing Date: Apr. 11, 2013.

* cited by examiner

METHOD FOR DISPERSION AND ADSORPTION COEFFICIENT ESTIMATION USING AN ANALYSIS OF PRESSURE TRANSITION DURING A VISCOSITY-SWITCH

RELATED APPLICATION

This application is related to, and claims priority to, U.S. Provisional Patent Application Ser. No. 61/624,074, filed on Apr. 13, 2012, the disclosure of which is incorporated by reference in its entirety.

BACKGROUND

1. Field of the Invention

Embodiments of the invention generally relate to dispersion and adsorption coefficient estimation, and more particularly, to methods for estimating porous-media longitudinal dispersion and adsorption coefficients through an analysis of pressure data during a viscosity switch between two solutions, one of which includes a viscosifying agent having a non-linear concentration-viscosity dependence. In accordance with certain embodiments, methods are also provided for estimating adsorption coefficients.

2. Description of the Related Art

Dispersion of miscible fluid flow in porous media has been investigated as a method for quantifying geological characterization and for defining reservoir heterogeneity for enhanced oil recovery (EOR). Conventional systems demonstrate that pore-scale heterogeneities exhibit local velocity variations. Due to these variations, not all solute particles move at a mean velocity; some move faster while others move slower, generating a distribution of solute spread about the mean velocity. This solute spreading (or smearing) is termed "mechanical" dispersion. Similarly, molecular diffusion also generates some smearing. The combined effect of mechanical dispersion and molecular diffusion is termed "microscopic" dispersion or in the context of a reservoir simulation, "physical" dispersion, to differentiate it from a "numerical" dispersion.

An understanding of dispersion of miscible fluid flow in a porous medium is important because dispersion governs the degree of mixing between different solutions and their respective phases. The degree of mixing is significant for various EOR processes. For surfactant EOR, for example, the degree of mixing governs a degree of emulsification and an associated interfacial tension (IFT) reduction. For polymer EOR, the degree of mixing between different salinity waters will govern the effectiveness of a polymer flood as salinity has a direct impact on polymers viscosibility. Therefore, an operator in the area of EOR would find it important to quantify the magnitude of physical dispersion for the optimization of EOR.

Some conventional dispersion estimation techniques involve the measurement of tracer-concentration smearing either in-situ or at a production outlet. In the former approach, an in-situ measurement, for example, nuclear magnetic resonance (NMR), is conducted, such that the spreading of an injected tracer can be tracked with time. The NMR data is then used to estimate a dispersion coefficient (see FIG. 1a). In the latter approach, produced effluents are analyzed to construct a tracer production profile that is fitted to a convection-diffusion equation (CDE) for deriving a dispersion coefficient estimate (see FIG. 1b). Thus, both of these conventional approaches require keeping track (i.e., measuring) of tracer concentrations across the production outlet to derive the injected concentration profile of the tracer(s) for determining the dispersion coefficient and the dispersivity of the porous medium (e.g., a reservoir rock).

SUMMARY

Embodiments of the invention are directed to methods for estimating porous-media longitudinal dispersion and adsorption coefficients through an analysis of pressure data during a viscosity-switch between two solutions. In accordance with various embodiments of the invention, one of the two solutions includes a viscosifying agent having a non-linear concentration-viscosity dependence.

In particular, in accordance with an embodiment of the invention, there is provided a method for estimating porous-media longitudinal dispersion coefficients, which includes introducing a pure phase component though a porous medium, and introducing a component having a same phase as the pure phase component through the porous medium. The component includes a viscosifying agent having a non-linear viscosity-concentration dependence. The method further includes measuring, using a permeability analyzer, a pressure drop across the porous medium after each introduction at a plurality of intervals over a period of time, and determining, using the measured pressure drops, a pressure transition across the porous medium. Each point along the pressure transition represents a difference between the measured pressure drops across the porous medium resulting from the introductions of the pure phase component and the component, at a respective interval over the period of time. Further, the method includes analyzing the pressure transition across the porous medium to determine a dispersion coefficient for the porous medium.

In accordance with another embodiment of the invention, there is provided a method for estimating porous-media longitudinal dispersion and adsorption coefficients, which includes introducing a first amount of a pure phase component through a porous medium, and introducing a component having a same phase as the pure phase component through the porous medium. The component includes a viscosifying agent having a non-linear viscosity-concentration dependence. The method further includes introducing a second amount of the pure phase component through the porous medium, measuring, using a permeability analyzer, a pressure drop across the porous medium after each introduction at a plurality of intervals over a period of time, and determining, using the measured pressure drops, a first pressure transition and a second pressure transition across the porous medium. Each point along the first pressure transition represents a difference between the measured pressure drops across the porous medium resulting from the introduction of the first amount of the pure phase component and the introduction of the component, at a respective interval over the period of time. Each point along the second pressure transition represents the difference between the measured pressure drops across the porous medium resulting from the introduction of the component and the introduction of the second amount of the pure phase component, at a respective interval over the period of time. Further, the method includes analyzing the first pressure transition and the second pressure transition across the porous medium to determine a dispersion coefficient and an adsorption coefficient for the porous medium.

BRIEF DESCRIPTION OF DRAWINGS

So that the manner in which the features and advantages of the invention, as well as others which will become apparent, may be understood in more detail, a more particular description of the invention briefly summarized above may be had by reference to the embodiments thereof which are illustrated in the appended drawings, which form a part of this specification. It is to be noted, however, that the drawings illustrate only various embodiments of the invention and are therefore not to be considered limiting of the invention's scope as it may include other effective embodiments as well.

FIGS. 15(a) and 15(b) demonstrate the corresponding relationship between the start-of, non-linear pressure transition, and the breakthrough, in accordance with an embodiment of the invention.

DETAILED DESCRIPTION

Figure 1B:
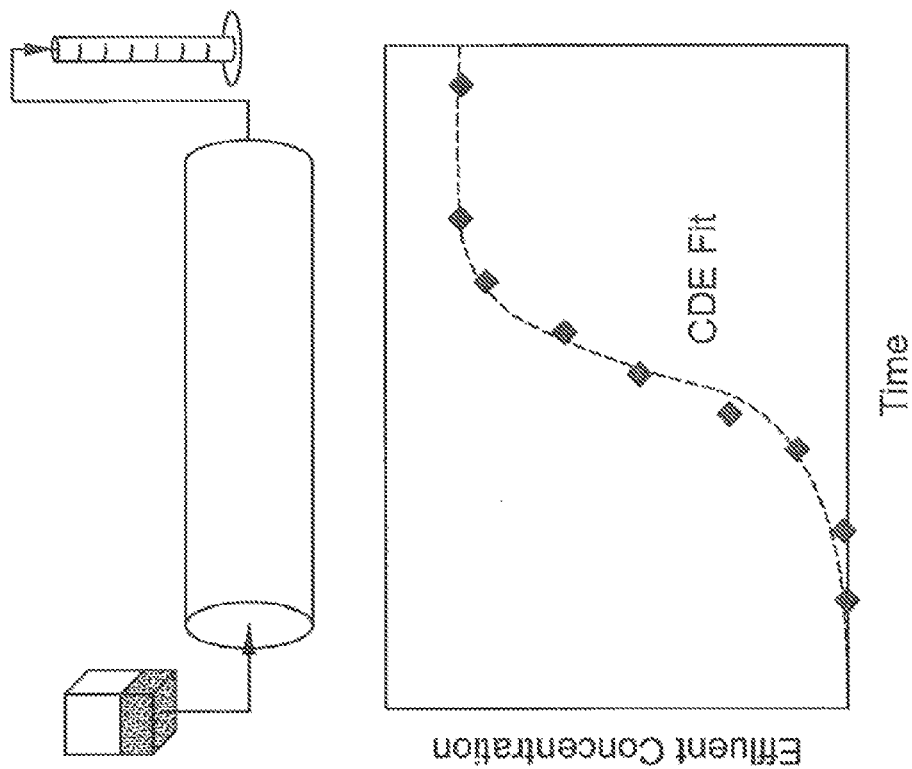
FIGS. 1(a) and (b) are graphs showing conventional dispersion-estimation techniques requiring measurement of an injected tracer concentration profile over time.
Figure 1A:
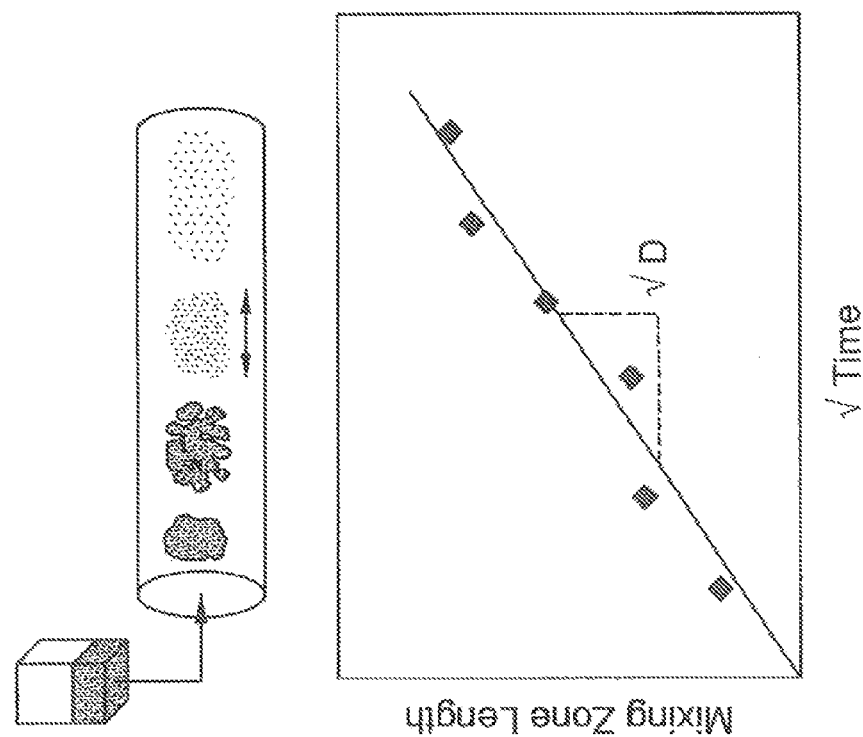

The present invention will now be described more fully hereinafter with reference to the accompanying drawings, which illustrate embodiments of the invention. This invention may, however, be embodied in many different forms and should not be construed as limited to the illustrated embodiments set forth herein. Rather, these embodiments are provided so that this disclosure will be thorough and complete, and will fully convey the scope of the invention to those skilled in the art. Like numbers refer to like elements throughout. Prime notation, if used, indicates similar elements in alternative embodiments.

Generally, embodiments of the invention are directed to methods for estimating porous-media longitudinal dispersion and adsorption coefficients through an analysis of pressure data during a viscosity-switch between two solutions. Embodiments of the invention demonstrate the effects of dispersion and adsorption on pressure transition, when a non-linear viscosifying agent is used to measure a pressure response between an introduction of a pure phase component (e.g., water) and an introduction of a component having the same phase saturated with the non-linear viscosifying agent (i.e., the components can be injected in either order). The pressure response is then analyzed to estimate dispersion in the porous media. According to certain embodiments of the invention, if the non-linear viscosifying agent adsorbs, then the methods can also be used to estimate the level of in-situ adsorption.

Conventional injectivity testing has been used in the context of polymer flooding to give an indication of potential injectivity issues, for example, providing estimates of polymer solution resistance and residual resistance. However, injectivity testing has not been used for dispersion estimation.

Embodiments of the invention, as will be discussed in detail below, demonstrate that dispersion and adsorption coefficients can be determined from the measurement of pressure responses between an introduction of a pure phase component (e.g., water) and an introduction of a component having the same phase saturated with a non-linear viscosifying agent. In certain embodiments, the non-linear viscosifying agent includes a non-sorbing agent for a determination of dispersion coefficients, while the non-linear viscosifying agent includes a sorbing agent for a determination of dispersion and adsorption coefficients. Embodiments further demonstrate that, for a sorbing agent, combining two cycles (i.e., pure-viscous-pure injection) reduces uncertainties in analyzing the pressure transition data.

In accordance with certain embodiments, for an irreversible sorbing agent, if the determination of only dispersion coefficients is desired, a viscous-pure injection cycle is performed such that adsorption effects are minimized.

The description of the following embodiments of the invention recognize that, for a linear viscosifying agent (i.e., linear viscosity concentration dependence) with no sorption, a pressure transition across the porous medium is directly linear beginning with the viscosity-switching point to a breakthrough point, with or without dispersion. For a linear viscosifying agent with dispersion, a non-linear pressure transition is observed post-breakthrough.

Furthermore, for a non-linear viscosifying agent, without dispersion, the pressure transition is observed to be directly linear. With dispersion, the non-linear viscosifying agent causes the pressure transition to be slower, and therefore post-breakthrough, the pressure transition is also observed to be non-linear. Adsorption is also demonstrated to slow the pressure transition.

In accordance with various embodiments, for a pure-viscous-pure injection scheme with dispersion and adsorption, a first pressure transition (i.e., between the introduction of a first pure water component and a water component including a non-linear viscosifying agent) is affected by both dispersion and adsorption. Whereas, a second pressure transition (i.e., between the introduction of the water component including the non-linear viscosifying agent and a second pure water component) is only affected by dispersion for the case associated with irreversible adsorption and is affected by both dispersion and adsorption for the case associated with reversible adsorption across the porous medium.

Figure 2:
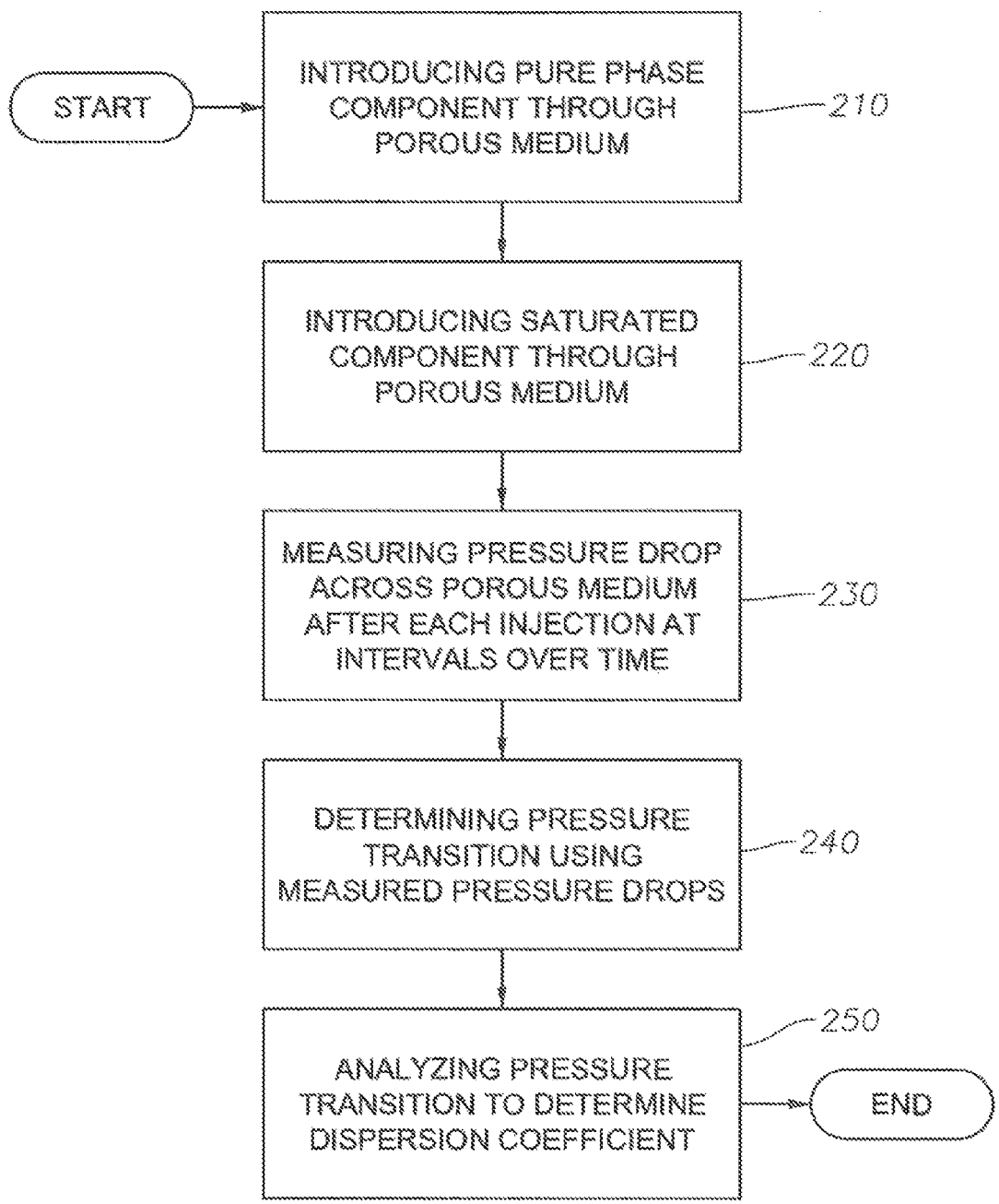
FIG. 2 is a flow diagram of a method estimating porous-media longitudinal dispersion coefficients through an analysis of a pressure transition during a viscosity-switch, in accordance with an embodiment of the invention.

As shown in FIG. 2, embodiments of the invention provide a method for estimating porous-media longitudinal dispersion coefficients. The method includes introducing, at step 210, a pure phase component, for example, water, though a porous medium, and introducing, at step 220, a component having a same phase as the pure phase component, for example, liquid, through the porous medium. In accordance with at least one embodiment, the component includes a viscosifying agent having a non-linear viscosity-concentration dependence. In accordance with a preferred embodiment, the component is saturated with the non-linear viscosifying agent. The component includes, for example, polymer-saturated water. The method further includes measuring, at step 230, using a permeability analyzer, a pressure drop across the porous medium after each introduction at a plurality of intervals over a period of time, and determining, at step 240, using the measured pressure drops, a pressure transition at each interval over the period of time. Each point along the pressure transition represents a difference between the measured pressure drops across the porous medium resulting from the introductions of the pure phase component and the component, at a respective interval over the period of time. Further, the method includes analyzing, at step 250, the pressure transition across the porous medium to determine a dispersion coefficient for the porous medium.

In accordance with various embodiments of the invention, the pressure transition can be analyzed using a number of analysis processes. For example, a numerical analysis involving numerical matching can be performed to determine the dispersion coefficient by matching the pressure transition to numerical predictions. Other analyses of the pressure transition include a best-fit analysis, such that the pressure transition is fitted to a convection-diffusion equation to estimate the dispersion coefficient, and a graphical analysis involving the analysis of pressure transition slopes against pre-constructed pressure transition-type curves.

In accordance with certain embodiments of the invention, the order of introducing the pure phase component and the component is interchangeable. In accordance with an embodiment of the invention, the dispersion coefficient is determined using a non-sorbing viscosifying agent in order to eliminate adsorption effects.

Figure 3:
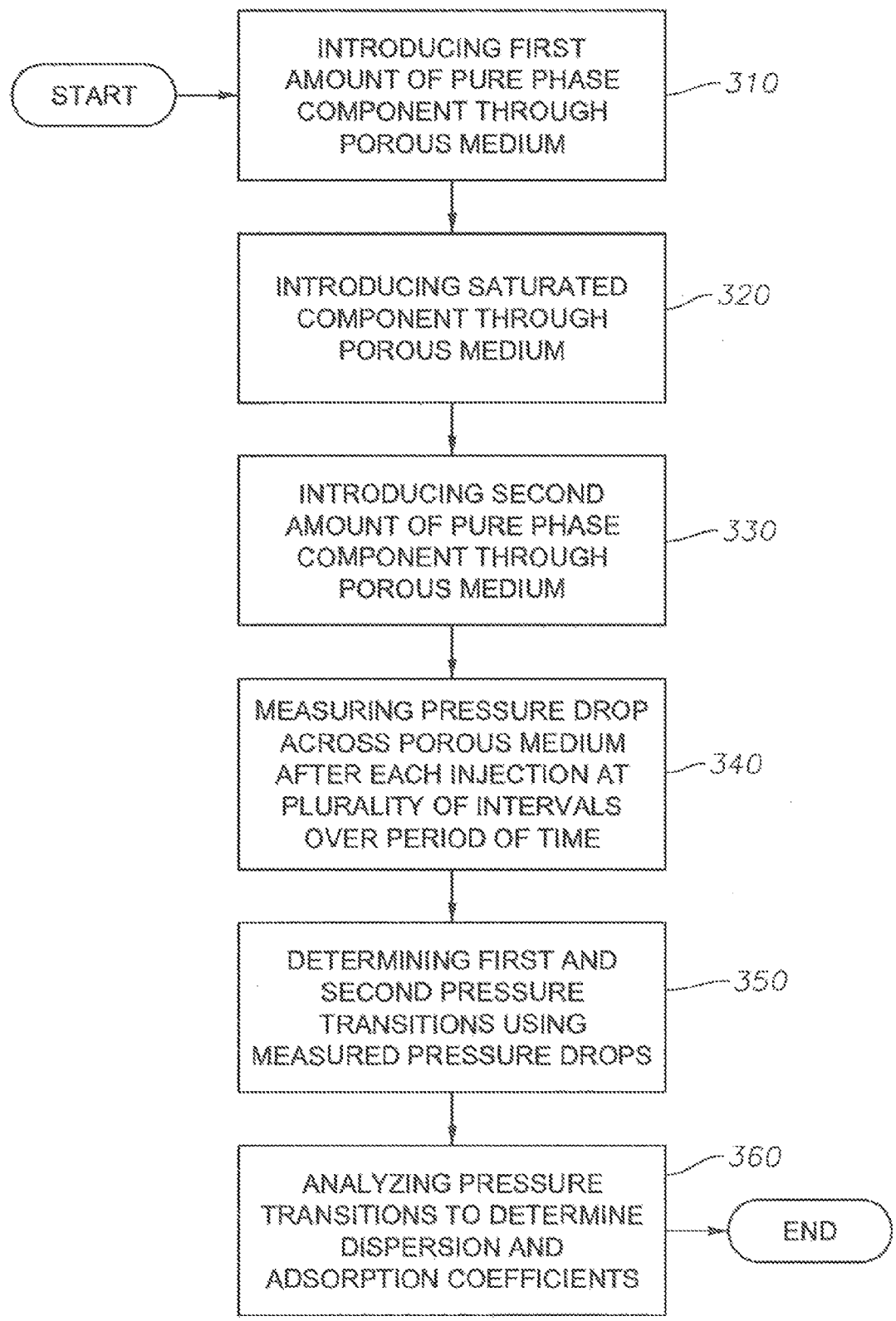
FIG. 3 is a flow diagram of a method estimating porous-media longitudinal dispersion and adsorption coefficients through an analysis of a pressure transition during a viscosity-switch, in accordance with an embodiment of the invention.

In accordance with another embodiment of the invention, there is provided a method for estimating porous-media longitudinal dispersion and adsorption coefficients. As shown in FIG. 3, the method includes introducing, at step 310, a first amount of a pure phase component, for example, water, though a porous medium, and introducing, at step 320, a component having a same phase as the pure phase component, for example, liquid, through the porous medium. In accordance with at least one embodiment, the component includes a viscosifying agent having non-linear viscosity-concentration dependence. In accordance with a preferred embodiment, the component is saturated with the non-linear viscosifying agent. The component includes, for example, polymer-saturated water. The method further includes introducing, at step 330, a second amount of the pure phase component through the porous medium, measuring, at step 340, using a permeability analyzer, a pressure drop across the porous medium after each introduction, at a plurality of intervals over a period of time, and determining, at step 350, using the permeability analyzer data, a first pressure transition and a second pressure transition. Each point along the first pressure transition represents a difference between the measured pressure drops across the porous medium resulting from the introduction of the first amount of the pure phase component and the introduction of the component, at a respective interval over the period of time. Each pressure drop along the second pressure transition represents the difference between the measured pressure drops across the porous medium resulting from the introduction of the first amount of the pure phase component, the introduction of the component, and the introduction of the second amount of the pure phase component, at a respective interval over the period of time. Further, the method includes analyzing, at step 360, the first pressure transition and the second pressure transition across the porous medium to determine a dispersion coefficient and an adsorption coefficient for the porous medium.

Figure 4:
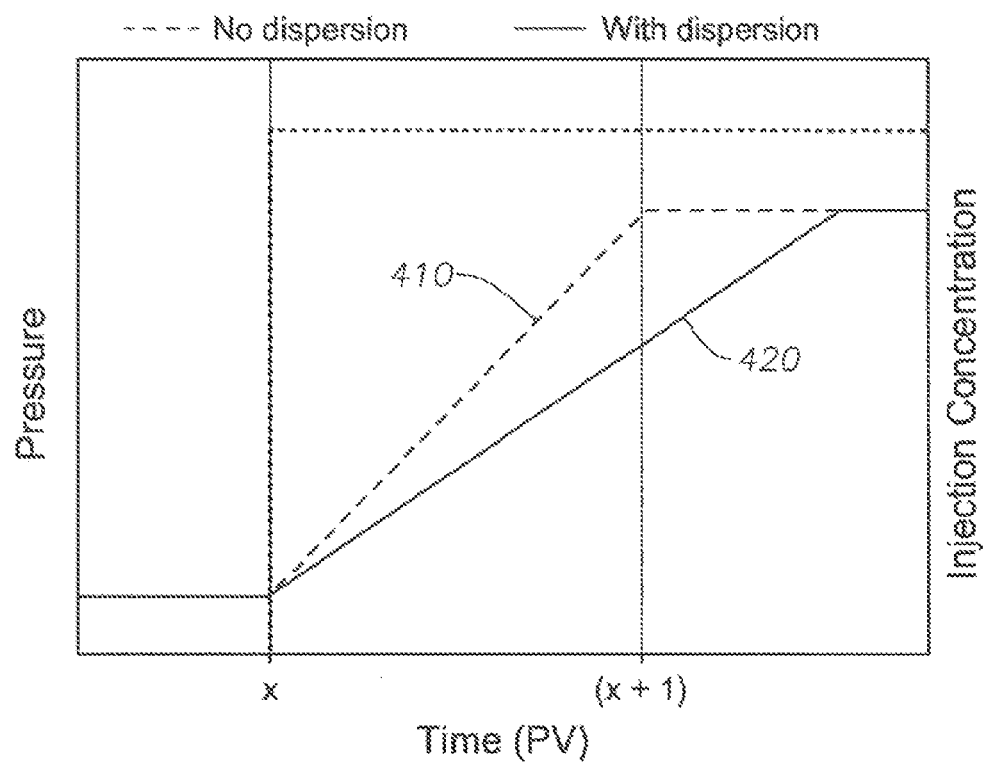
FIG. 4 is a graph showing the effect of dispersion on a pressure propagation between pure and viscous water injections with and without a non-linear viscosifying agent, in accordance with an embodiment of the invention.

Embodiments of the invention demonstrate that the viscosity transition between the introduced pure phase component and the introduced component having the same phase saturated with the viscosifying agent will result in a pressure transition. A non-linear viscosifying agent—without dispersion—will have a pressure transition identical to a linear viscosifying agent. With dispersion, a non-linear viscosifying agent would distort the pressure transition from that of a linear viscosifying agent. FIG. 4 is a graph showing the effect of dispersion on a pressure propagation between pure and viscous water introductions with and without a non-linear viscosifying agent, in accordance with an embodiment of the invention. As shown in FIG. 4, without dispersion, the pressure transition is directly linear with respect to time (410). However, with dispersion, due to the non-linearity of the viscosity-concentration dependence of the viscosifying agent, the pressure transition will further spread (i.e., take more times to propagate) (FIG. 4, 420). According to certain embodiments of the invention, adsorption of the viscosifying agent also can cause a similar effect where the pressure propagation is delayed. Nevertheless, these effects can be decoupled either through: (1) recognizing the difference between dispersion and adsorption imprints on pressure propagation, or (2) starting with viscous water followed by the introduction of pure water.

Intuitively, the flow of a more viscous solution results in an increase in pressure drop compared to a less viscous solution. This increase according to Darcy's Law should be proportional to the viscosity ratio of the solutions, as shown in Equation (1):

$$\frac{\Delta P_2}{\Delta P_1} = \frac{\mu_2}{\mu_1} \qquad (1)$$

where $\Delta P$ is a pressure drop and $\mu$ is viscosity, with subscripts "1" and "2" referring to the pure and more viscous solutions, respectively. This equation applies once the displacement reaches steady state; that is for cores fully saturated with a single solution: $C/C_o=0$ or 1 across the core.

Immediately after the initiation of the viscous (or pure—can be in either order) introduction, the pressure drop undergoes a transition between the two pressure drops: $\Delta P_1$ to $\Delta P_2$ (or $\Delta P_2$ to $\Delta P_1$). According to various embodiments of the invention, the pressure drop reaches the plateau once the core is fully saturated with the viscous (or pure) solution. Thus, as further shown in FIG. 4 for the case without sorption (i.e., retardation) and dispersion, the pressure drop reaches a plateau after the injection of 1 pore-volume (PV).

Figure 5:
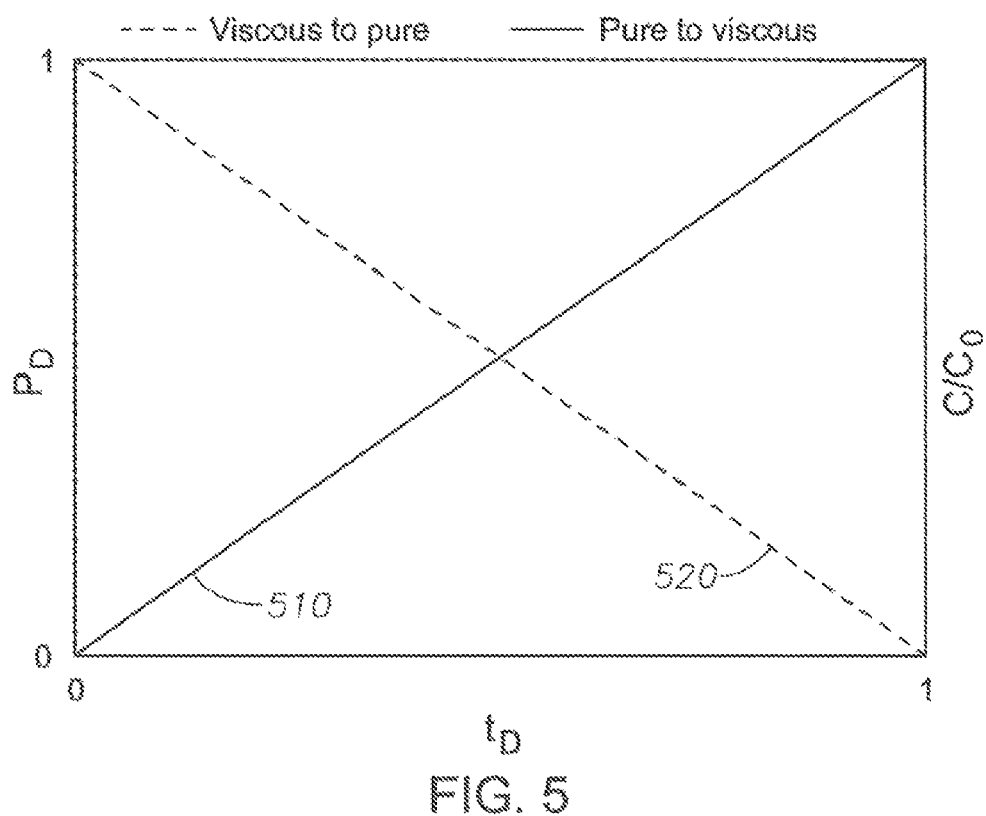
FIG. 5 is a graph showing a dimensionless plot of a pressure drop transition during a viscosity-switch for a case with no dispersion or retardation, in accordance with an embodiment of the invention.

FIG. 5 is a graph showing a dimensionless plot of a pressure drop transition, $P_D$, during a viscosity-switch for a case with no dispersion or retardation, in accordance with an embodiment of the invention. As shown in FIG. 5, the pressure drop transition has a slope of 1 (510) on a dimensionless pressure/time plot for the case where the pressure drop reaches a plateau once the core is fully saturated with the viscous solution (i.e., pure to viscous), and a slope of −1 (520) on the plot for the case where the pressure drop reaches a plateau once the core is fully saturated with the pure solution (i.e., viscous to pure).

Figure 6:
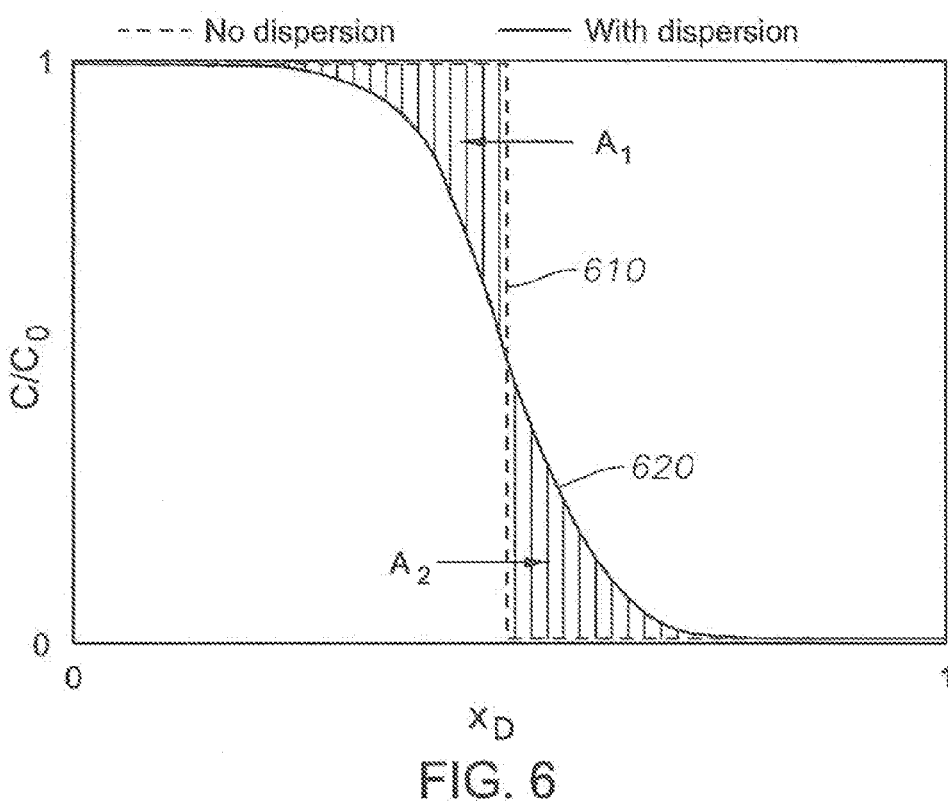
FIG. 6 is a graph showing the effect of dispersion on the viscosity of a polymer front that due to dispersion is smeared with retarded and accelerated portions, in accordance with an embodiment of the invention.

FIG. 6 is a graph showing the effect of dispersion on the viscosity of a polymer front that due to dispersion is smeared with retarded and accelerated portions, in accordance with an embodiment of the invention. As shown in FIG. 6, for the case without dispersion, the concentration propagates as a shock, and as the concentration propagation advances, the overall viscosity across the core changes linearly between the two viscosity extremes (610). As a result, the pressure transition is also linear. In the case with dispersion, the concentration front is smeared, such that two distinct portions are present: retarded and accelerated (see FIG. 6, A1 and A2, respectively) (620). Consequently, since the solution viscosity is a function of concentration, dispersion also affects the overall viscosity across the core, thus affecting the pressure transition, as shown in FIG. 6.

Figure 7A:
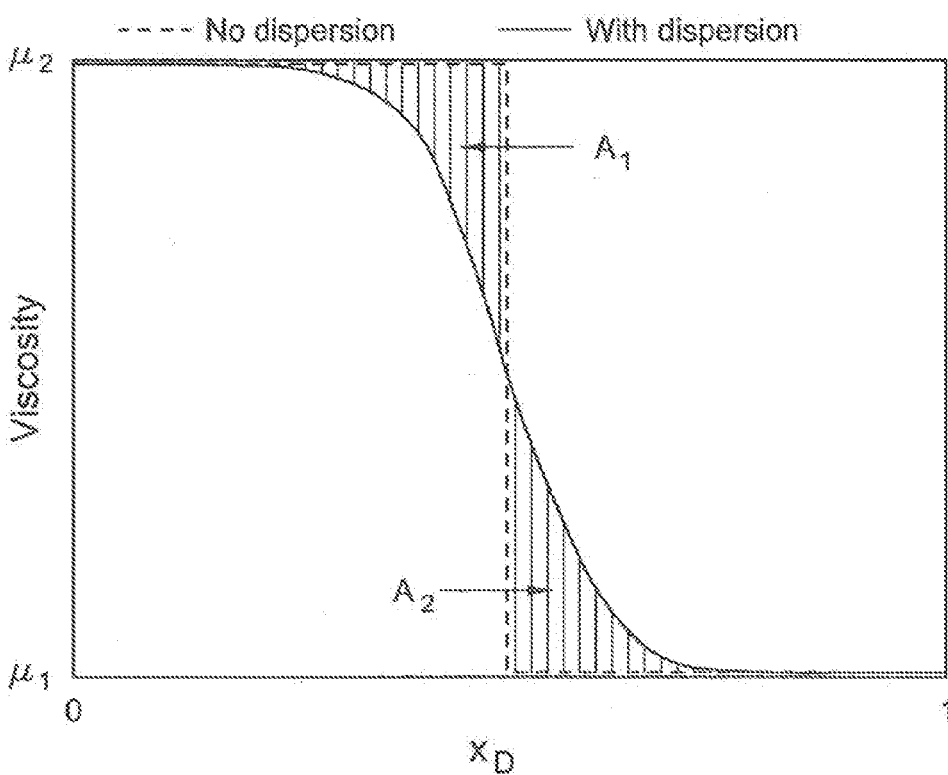
FIGS. 7(a) and (b) are graphs showing the dispersion effect on the viscosity profile (hence, the overall viscosity and the pressure drop) for (a) linear and (b) non-linear viscosifying agents, in accordance with an embodiment of the invention.
Figure 7B:
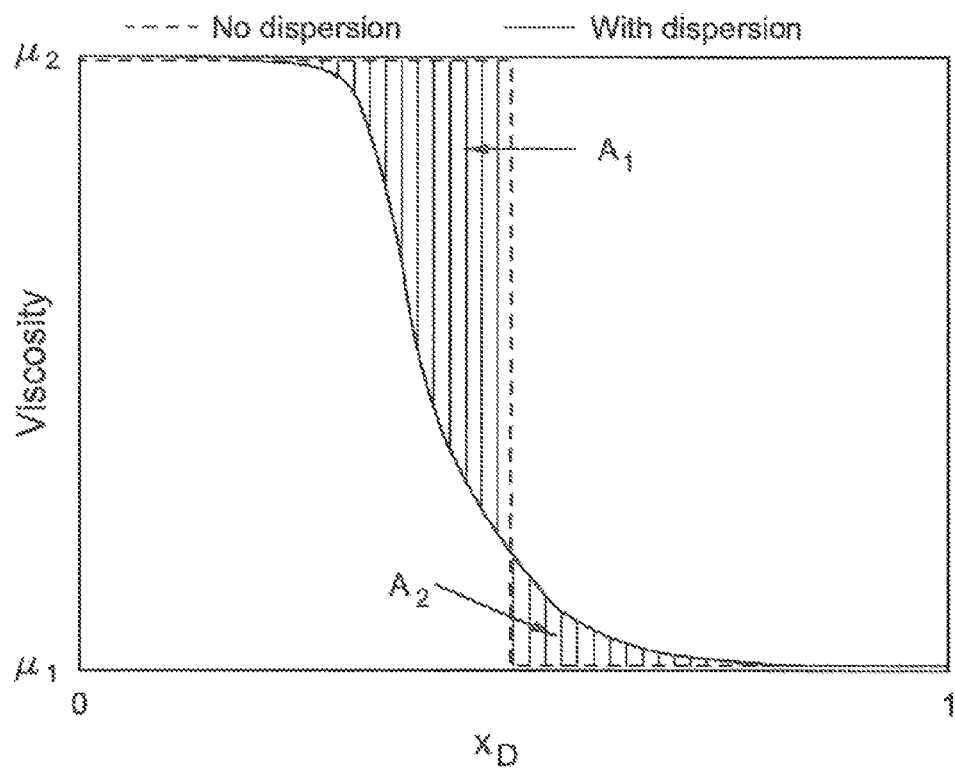
Figure 8:
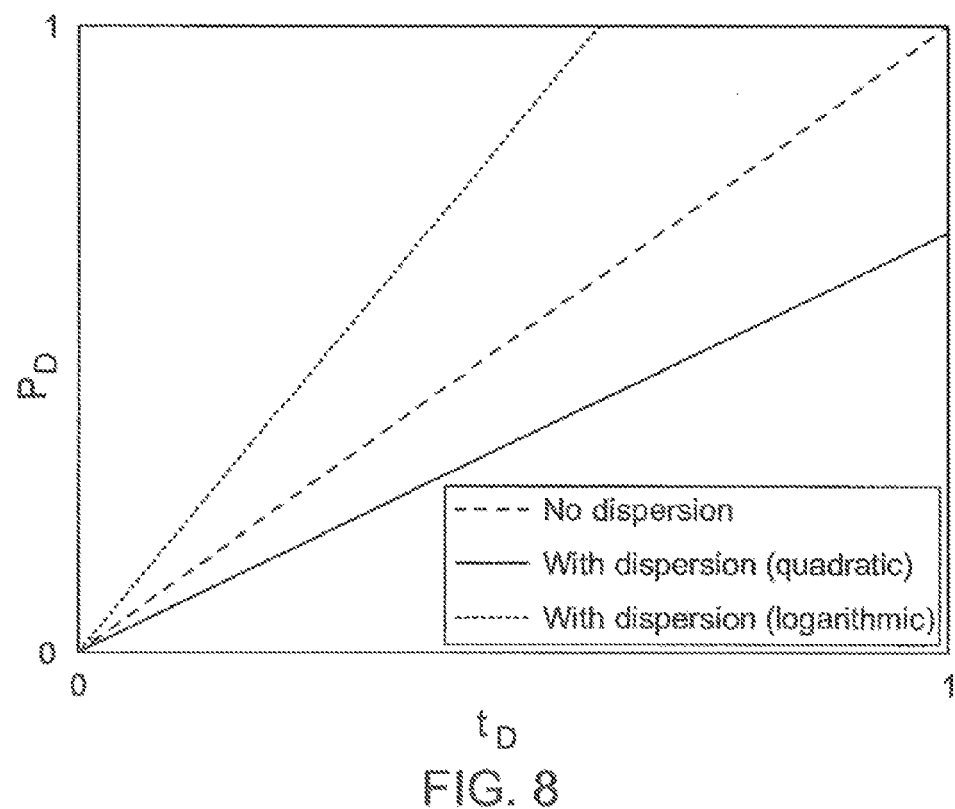
FIG. 8 is a graph showing the dispersion effect on the pressure drop transition for non-linear viscosifying agents, in accordance with an embodiment of the invention.
Figure 9A:
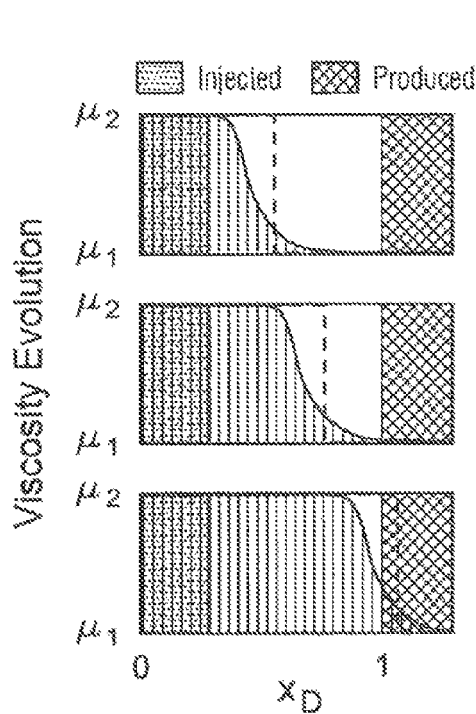
FIGS. 9(a) to (c) are graphs showing a viscosity evolution with time, with and without dispersion, and the dispersion effect on the pressure drop transition, in accordance with an embodiment of the invention.
Figure 9B:
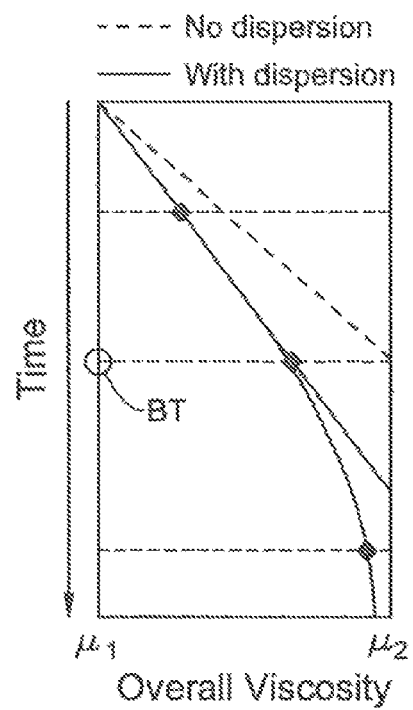
Figure 9C:
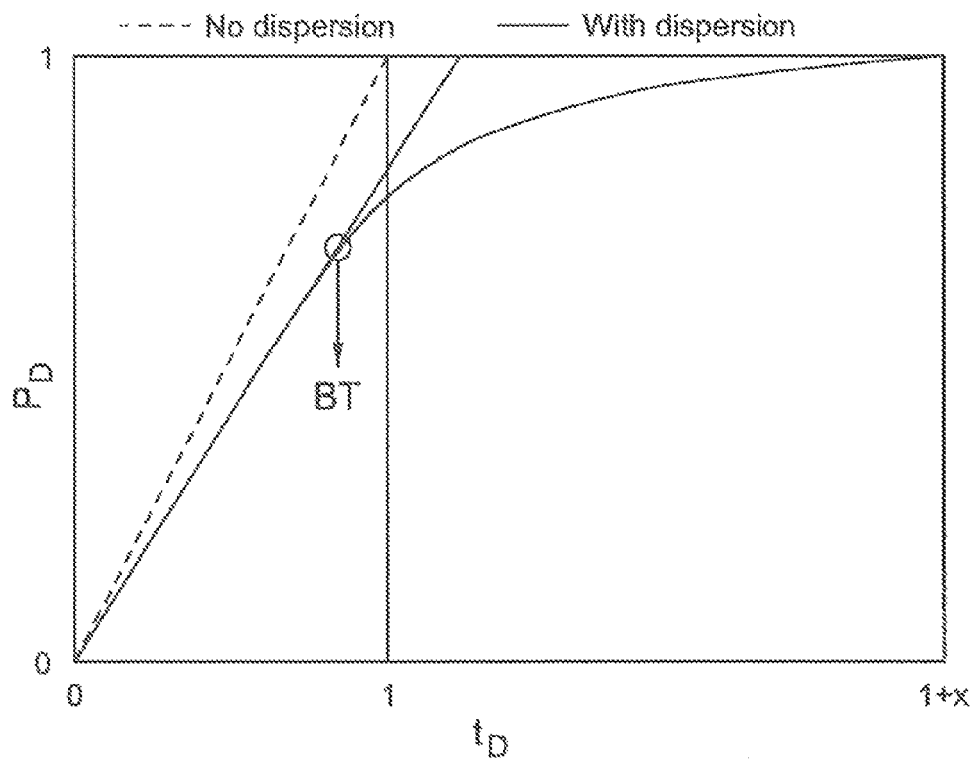

FIGS. 7(a) and (b) are graphs showing a dispersion effect on a viscosity profile (e.g., the overall viscosity and the pressure drop) for (a) linear and (b) non-linear viscosifying agents, in accordance with an embodiment of the invention. As shown in FIG. 7(a), if the viscosity-concentration dependence is linear then viscosity losses, $A_1$, across the retarded section are balanced by viscosity gains, $A_2$, across the accelerated section. Nevertheless, if a non-linear viscosifying agent is injected, viscosity losses and gains will no longer balance. For example, as shown in FIG. 7(b), if the viscosity-concentration dependence is quadratic, then viscosity losses across the retarded section will outweigh viscosity gains, and therefore the overall viscosity is lower at any point during the pressure transition. Because the viscosity is lower, the transition between the two pressure drops is slower, as shown in FIG. 8. As further shown in FIG. 8, with dispersion the pressure drop transition on a dimensionless pressure/time plot is still a linear line, but has a slope less than 1. The y-endpoint-intercept (at $t_D=1$) gives a direct indication about the level of dispersion in the porous medium. However, as the viscosifying agent front reaches the production outlet, the pressure drop transition deviates from linearity, as shown in FIGS. 9(a)-(c). FIGS. 9(a)-(c) show that dispersion effect causes the overall viscosity shift to lessen and the pressure drop transition) to slow down and deviate from linearity.

According to certain embodiments of the invention, the viscosifying agent also deviates from linearity at the onset of viscous injection, while the smeared front develops. Although the discussion above was presented for a pure-to-viscous injection cycle, certain embodiments demonstrate that similar conclusions apply for a viscous-to-pure cycle.

Figure 10A:
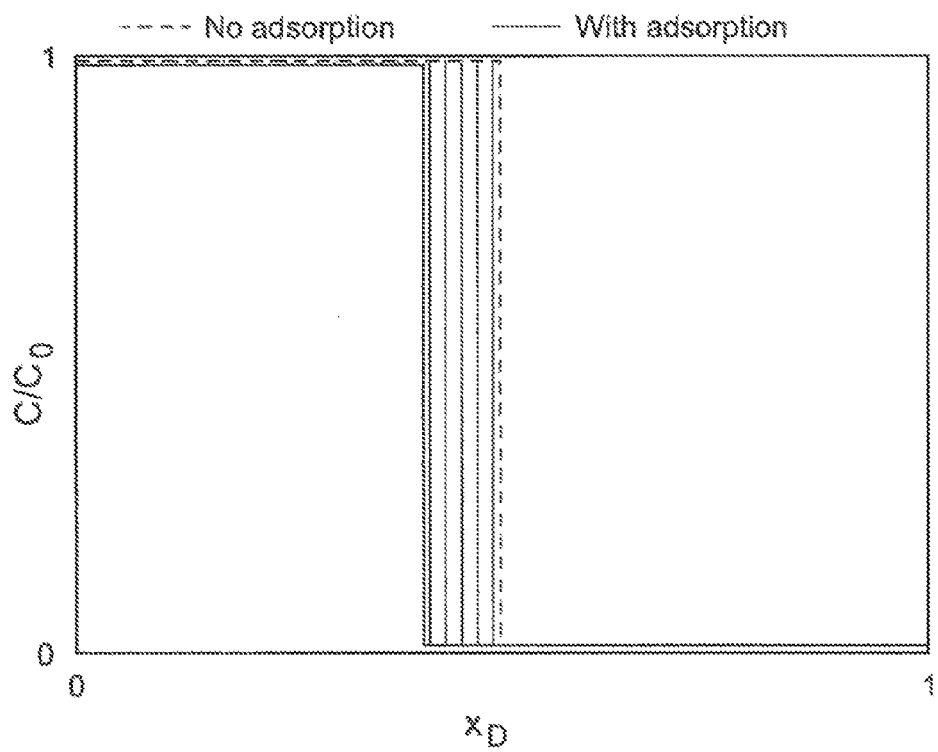
FIGS. 10(a) and (b) are graphs showing the effect of adsorption on (a) a concentration profile and (b) a pressure transition, in accordance with an embodiment of the invention.
Figure 10B:
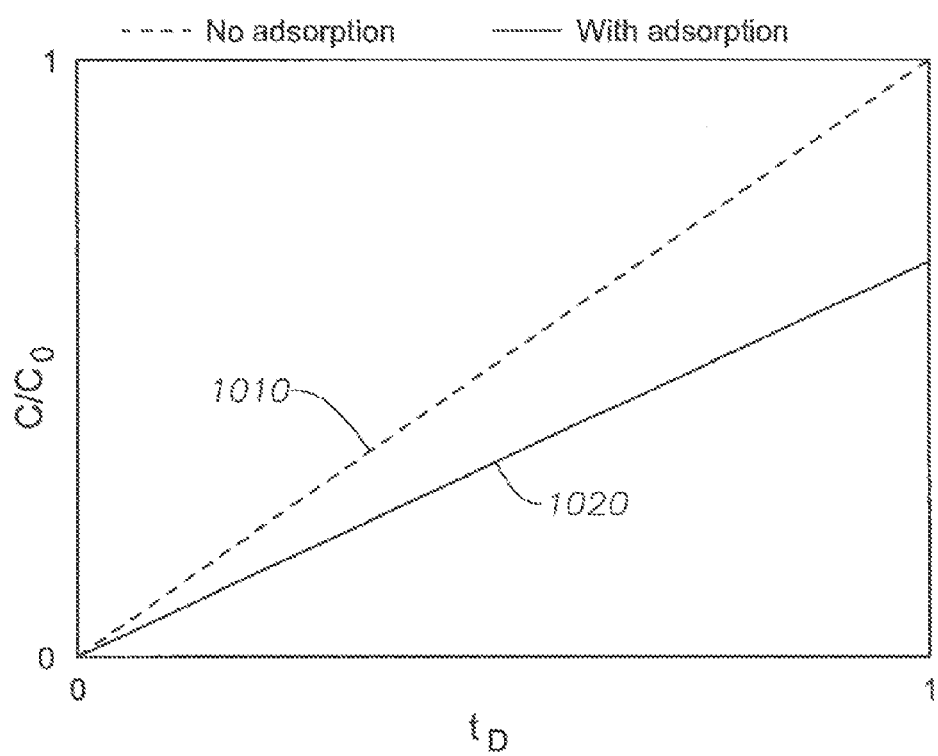

FIGS. 10(a) and (b) are graphs showing the effect of adsorption on (a) a concentration profile and (b) a pressure transition, in accordance with an embodiment of the invention. As shown in FIG. 10(a), if the viscosifying agent adsorbs to the rock surface, adsorption will result in the retardation of the polymer front. In accordance with various embodiments, the retardation builds up with time as more and more polymer gets adsorbed. Therefore, without dispersion, adsorption results in a slow, linear pressure transition regardless of the adsorption isotherm. FIG. 10(b) shows the expected pressure transition with (1010) and without (1020) adsorption. As for dispersion, the y-intercept on the dimensionless pressure/time plot represents the adsorption level. However, without dispersion, adsorption should not result in any non-linearity.

Additionally, opposed to dispersion, adsorption affects both non-linear and linear viscosifying agents. According to certain embodiments, if irreversible, adsorption would not affect a viscous-to-pure injection cycle.

Experimentation

According to various embodiments of the invention, the effectiveness of a polymer injectivity test to estimate dispersion relies on the non-linearity of viscosity-concentration dependence of a viscosifying agent. For polymers, this non-linearity holds above the overlap concentration. Moreover, in injectivity tests, two pressure transitions take place. In the first, as water is switched to viscous flooding, both adsorption and dispersion affect the pressure propagation, while in the second, as the polymer is switched to water flooding, only dispersion is a factor. For these reasons, the following examples are demonstrated based on analyzing polymer injectivity test data.

Using single-phase coreflooding, injectivity data was measured for a polymer (e.g., a polyacrylamide solution) in a limestone core for estimating the longitudinal dispersivity and sorption of the limestone rock through an analysis of a pressure transition during a viscosity-switch between pure water and a polyacrylamide solution-saturated water. The properties of the rock and fluid polymer are listed in Table 1.

TABLE 1

| Fluid and rock properties for the injectivity test | | | | |
|---|---|---|---|---|
| Fluid Properties | | | | |
| Water viscosity | , | $\mu_w$ | : 0.36 | mPa · s |
| Polymer viscosity | , | $\mu(C_o)$ | : 7.7 | mPa · s |
| Rock Properties | | | | |
| Permeability | , | k | : 89 | md |
| Porosity | , | $\phi$ | : 0.23 | |

Figure 11:
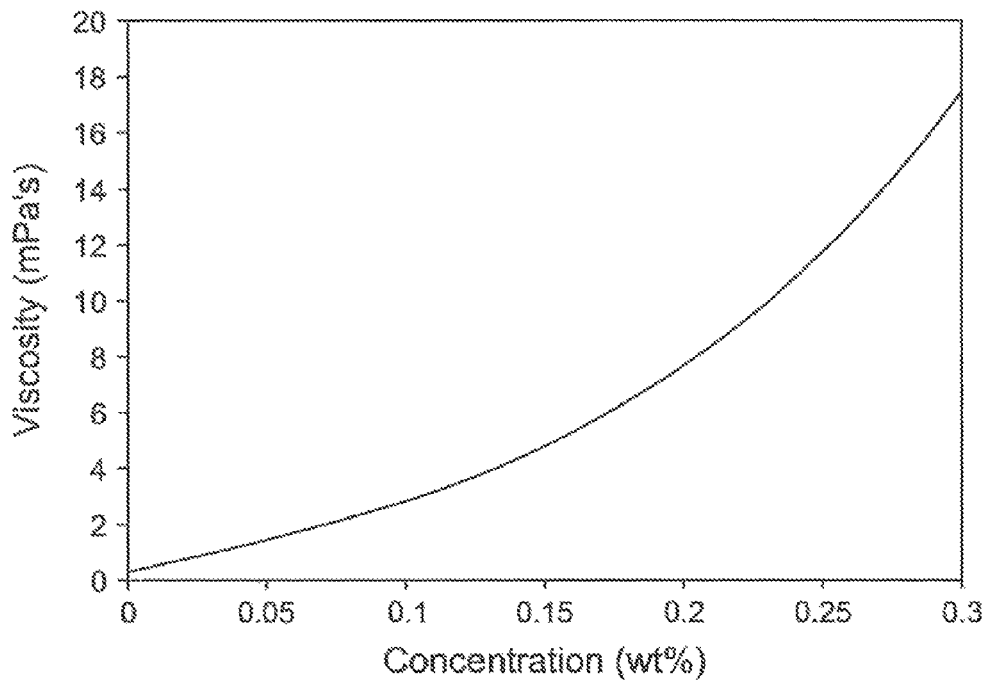
FIG. 11 is a graph showing the viscosity-concentration dependence of a polymer (e.g., a polyacrylamide solution), in accordance with an embodiment of the invention.
Figure 12:
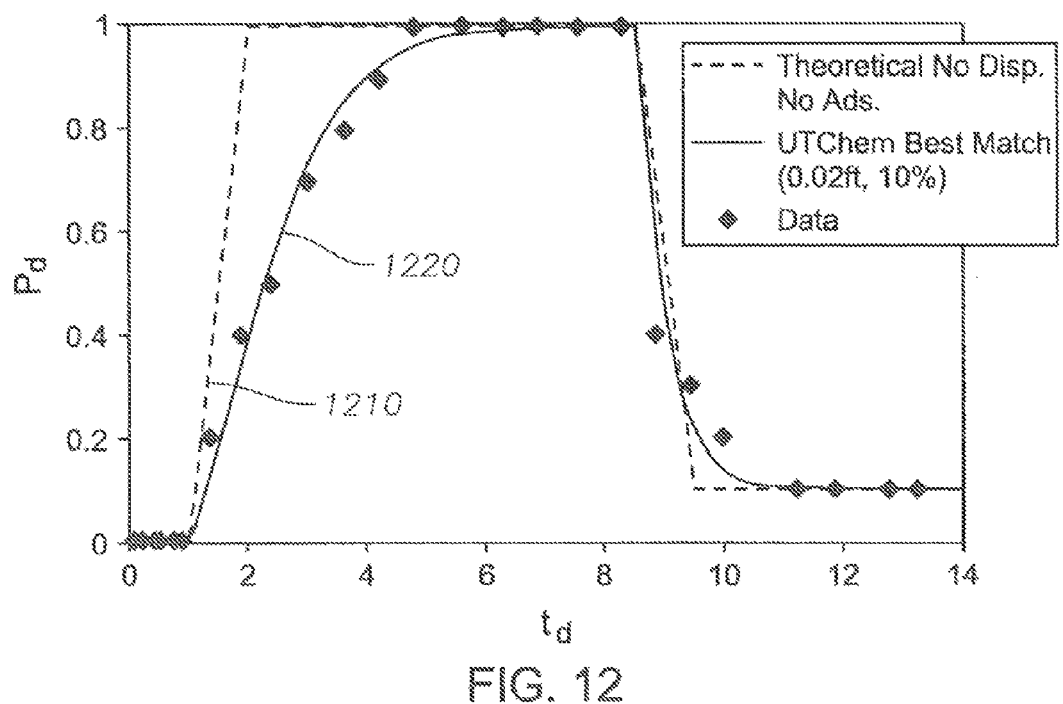
FIG. 12 is a graph showing injectivity results fitted using a chemical flood simulator to estimate dispersion and adsorption, in accordance with an embodiment of the invention.

FIG. 11 is a graph showing the viscosity-concentration dependence of a polymer (e.g., the polyacrylamide solution), in accordance with an embodiment of the invention. In the injectivity test, 1 PV of pure water was injected through the limestone rock, followed by an injection of the polyacrylamide solution at a concentration of 0.2 weight percent. After an injection of 7.5 PVs of the polyacrylamide solution, pure water was re-injected. FIG. 12 is a graph showing injectivity results fitted using a chemical flood simulator to estimate dispersion and adsorption, in accordance with an embodiment of the invention. The results for the experiment discussed above for FIG. 11 are shown in FIG. 12 along a theoretical pressure transition without adsorption and dispersion (1210). In accordance with an embodiment of the invention, the chemical flood simulator simulates EOR using surfactant and polymer processes (1220). In accordance with one embodiment, the simulator is a 3-D, multicomponent, multiphase, compositional model of chemical flooding processes, which accounts for complex phase behavior, chemical and physical transformations and heterogeneous porous media properties, and uses advanced concepts in high-order numerical accuracy and dispersion control and vector and parallel processing, as a non-limiting example. One of ordinary skill in the relevant art would have understood that other simulators would be contemplated for various embodiments of the invention. In accordance with at least one embodiment, the simulator includes a two-phase, three-component polymer-flooding-type simulator that accounts for/models polymer adsorption and polymer non-linear viscosity-concentration relationships.

Figure 13:
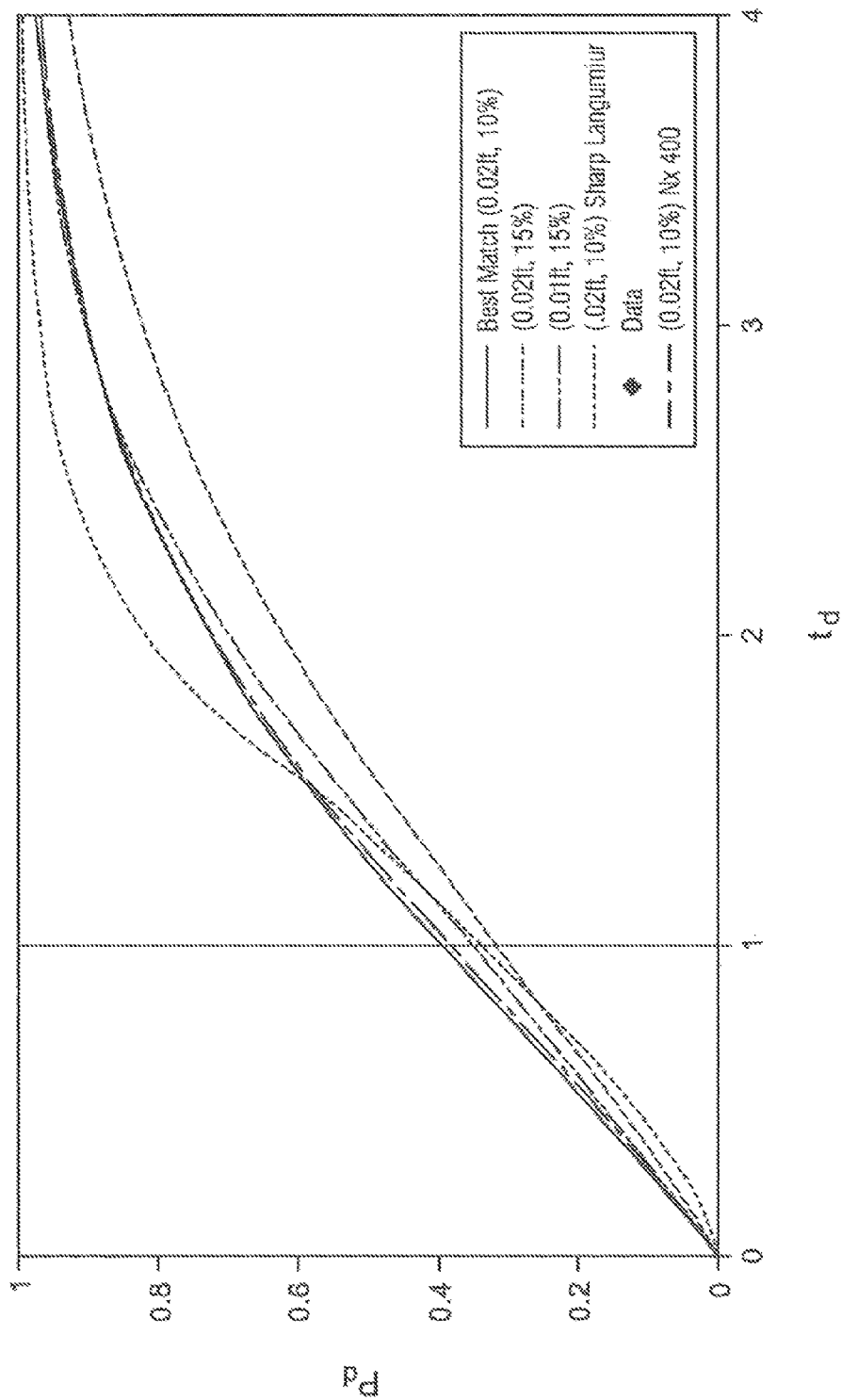
FIG. 13 is a graph showing dispersion and adsorption sensitivity results around a best fit, in accordance with an embodiment of the invention.

FIG. 12 shows a best simulation-based fit. In accordance with one embodiment, the best fit was obtained using a longitudinal dispersivity of 0.02 ft and an adsorption level of 10%. For this run, a 40-cells model was used in which $\Delta x$ was 0.002534 ft, i.e., a numerical dispersivity in the order of $\frac{1}{2}\Delta x$ for single-point-upstream weighting (e.g., approximately 0.0013 ft). Given the use of a total-variation-dimensioning scheme in the chemical flood simulator, numerical dispersion is swamped by physical dispersion, and thus can be ignored. This was verified by performing a sensitivity run using a finer model where the results were identical, as shown in FIG. 13. In particular, FIG. 13 is a graph showing dispersion and adsorption sensitivity results around a best fit, in accordance with an embodiment of the invention.

Figure 14A:
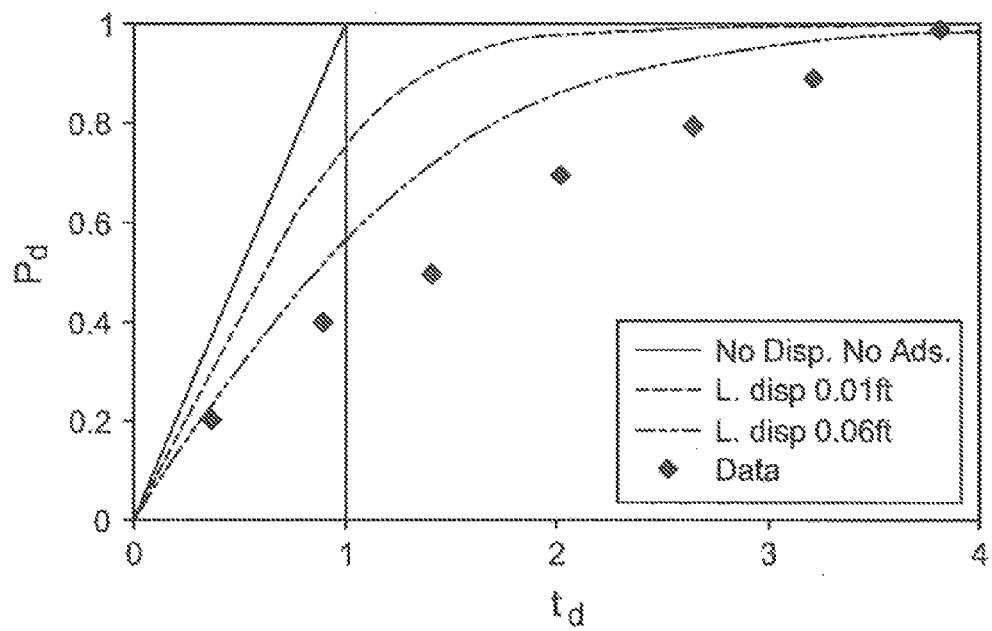
FIGS. 14(a) and (b) show a relationship between the independent effects of dispersion and adsorption, respectively, as predicted by a simulation against experimental data, in accordance with an embodiment of the invention.
Figure 14B:
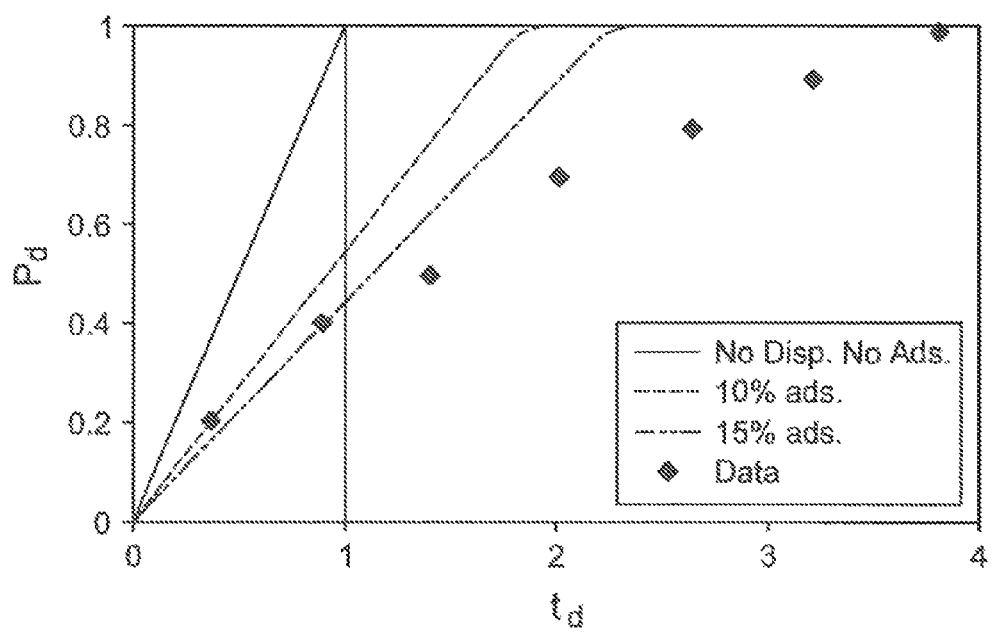

In accordance with certain embodiments, experimentation was conducted to investigate the independent effect of adsorption and dispersion on the pressure transition between the two solutions, one of which includes a viscosifying agent having a non-linear concentration-viscosity dependence. In particular, FIGS. 14(a) and (b) show a relationship between the independent effects of dispersion and adsorption, respectively, as predicted by a simulation against experimental data, in accordance with an embodiment of the invention. As shown in FIGS. 14(a) and (b), without adsorption, high dispersivity is required to obtain a reasonable match to the pressure transition data. On the other hand, without dispersion, adsorption can only fit the initial transition period, but cannot predict the non-linear transition at the end time. Simulation results validate the results that collectively adsorption and dispersion produce a slower pressure transition between the solutions, and thus the higher the adsorption or dispersion, the slower the pressure transition between the two solutions.

Figure 15A:
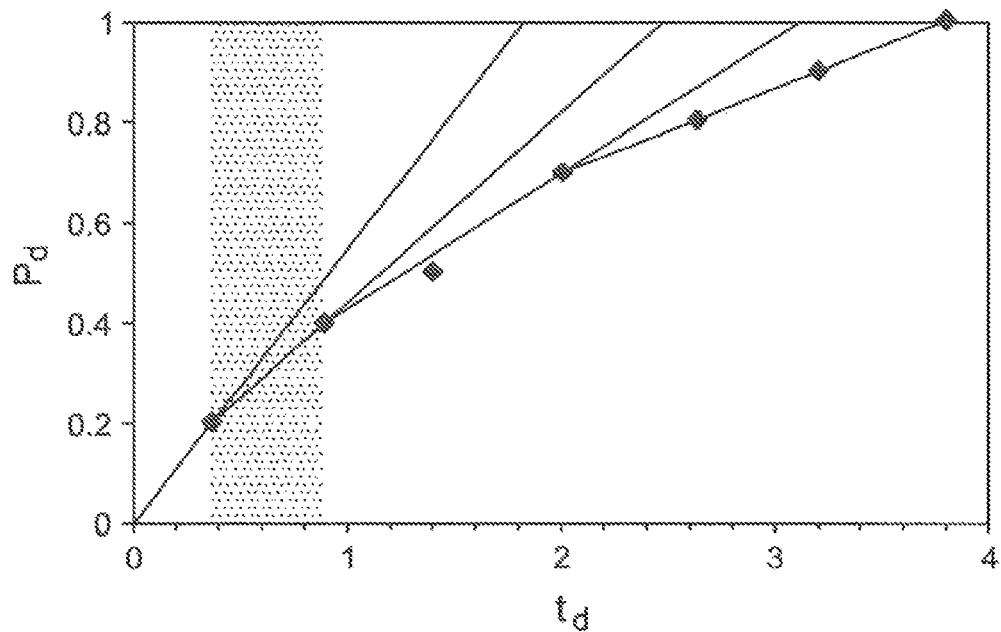
FIG. 15(a) shows a graph of the non-linearity of the pressure transition based on experimental data.
Figure 15B:
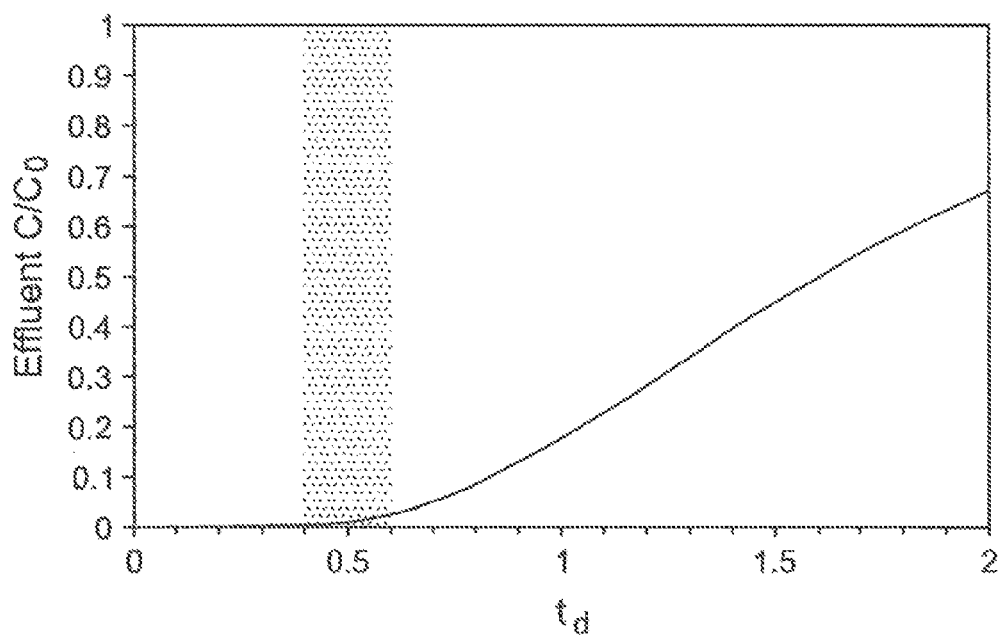
FIG. 15(b) shows a graph of the normalized effluent concentration profile, as predicted by a chemical flood simulator using the estimated adsorption and dispersion parameters shown in FIGS. 12 and 13.

FIG. 15(a) shows a graph of the non-linearity of the pressure transition based on experimental data, and FIG. 15(b) shows a graph of the normalized effluent concentration profile, as predicted by a chemical flood simulator using the estimated adsorption and dispersion parameters shown in FIGS. 12 and 13. FIGS. 15(a) and 15(b) demonstrate the corresponding relationship between the start-of, non-linear pressure transition and the breakthrough, in accordance with an embodiment of the invention.

The present invention may suitably comprise, consist or consist essentially of the elements disclosed and may be practiced in the absence of an element not disclosed. For example, it can be recognized by those skilled in the art that certain steps can be combined into a single step.

Unless defined otherwise, all technical and scientific terms used have the same meaning as commonly understood by one of ordinary skill in the art to which this invention belongs.

The singular forms "a," "an," and "the" include plural referents, unless the context clearly dictates otherwise.

As used herein and in the appended claims, the words "comprise," "has," and "include" and all grammatical variations thereof are each intended to have an open, non-limiting meaning that does not exclude additional elements or steps.

"Optionally" means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

Although the present invention has been described in detail, it should be understood that various changes, substitutions, and alterations can be made hereupon without departing from the principle and scope of the invention. Accordingly, the scope of the present invention should be determined by the following claims and their appropriate legal equivalents.

What is claimed is:

1. A method for estimating porous-media longitudinal dispersion coefficients, the method comprising:
   introducing a pure phase component though a porous medium;
   introducing a component having a same phase as the pure phase component through the porous medium, the component comprising a viscosifying agent;
   measuring, using a permeability analyzer, a pressure drop across the porous medium after each introduction at a plurality of intervals over a period of time;
   determining, using the measured pressure drops, a pressure transition, each point along the pressure transition representing a difference between the measured pressure drops across the porous medium resulting from the introductions of the pure phase component and the component at a respective interval over the period of time; and
   analyzing the pressure transition across the porous medium to determine a dispersion coefficient for the porous medium.

2. The method of claim 1, wherein the pure phase component comprises water and the component comprises a polymer-saturated water.

3. The method of claim 2, wherein the polymer-saturated water comprises polyacrylamide solution.

4. The method of claim 1, wherein the viscosifying agent has a non-linear viscosity-concentration dependence.

5. The method of claim 1, wherein the analyzing the pressure transition comprises one of a numerical analysis selected from the group consisting of numerical matching, such that the dispersion coefficient is determined by matching the pressure transition to numerical predictions, a best fit analysis, such that the pressure transition is fitted to a convection-diffusion equation to estimate the dispersion coefficient, and a graphical analysis involving the analysis of pressure transition slopes against pre-constructed pressure transition-type curves.

6. The method of claim 1, wherein the introducing the component comprises introducing the component comprising a non-sorbing viscosifying agent.

7. The method of claim 1, wherein an order of the introduction of the pure phase component and the introduction of the component through the porous medium is interchangeable.

8. A method for estimating porous-media longitudinal dispersion and adsorption coefficients, the method comprising:

introducing a first amount of a pure phase component though a porous medium;

introducing a component having a same phase as the pure phase component through the porous medium, the component comprising a viscosifying agent having a non-linear viscosity-concentration dependence;

introducing a second amount of the pure phase component through the porous medium;

measuring, using a permeability analyzer, a pressure drop across the porous medium after each introduction at a plurality of intervals over a period of time;

determining, using the measured pressure drops, first pressure transition and a second pressure transition, each point along the first pressure transition representing a difference between the measured pressure drops across the porous medium resulting from the introduction of the first amount of the pure phase component and the introduction of the component, and each point along the second pressure transition representing the difference between the measured pressure drops across the porous medium resulting from the introduction of the component and the introduction of the second amount of the pure phase component; and analyzing the first pressure transition and the second pressure transition across the porous medium to determine a dispersion coefficient and an adsorption coefficient for the porous medium.

9. The method of claim 8, wherein the pure phase component comprises water and the component comprises a polymer-saturated water.

10. The method of claim 9, wherein the polymer-saturated water comprises polyacrylamide solution.

11. The method of claim 8, wherein the analyzing the first and the second pressure transitions comprises one of a numerical analysis selected from the group consisting of numerical matching, such that the dispersion and adsorption coefficients are determined, by matching the first and the second pressure transitions to numerical predictions, a best fit analysis, such that the first and the second pressure transitions are fitted to a convection-diffusion equation to estimate the dispersion and adsorption coefficients, and a graphical analysis involving the analysis of first and the second pressure transition slopes against pre-constructed pressure transition-type curves.

12. The method of claim 8, wherein the introducing the component comprises introducing component comprising a non-sorbing viscosifying agent.

13. The method of claim 8, wherein an order of the introduction of the first amount and the second amount of the pure phase component and the introduction of the component through the porous medium is interchangeable.

* * * * *

UNITED STATES PATENT AND TRADEMARK OFFICE
CERTIFICATE OF CORRECTION

PATENT NO.         : 9,200,996 B2
APPLICATION NO.    : 13/861147
DATED              : December 1, 2015
INVENTOR(S)        : Abdulkareen Mohamad AlSofi Page 1 of 1

It is certified that error appears in the above-identified patent and that said Letters Patent is hereby corrected as shown below:

In the Claims

In Column 11, Line 12, Claim 8, the last three words appear as "drops, first pressure" and should read --drops, a first pressure--.

In Column 12, Line 11, Claim 11, the third word appears as "determined," and should read --determined--.

Signed and Sealed this
Eighth Day of March, 2016

Michelle K. Lee
*Director of the United States Patent and Trademark Office*